United States Patent [19]

Mihailovski et al.

[11] 3,998,880
[45] Dec. 21, 1976

[54] PRODUCTION OF N,N-DIETHYL 2(α-NAPHTHOXY)PROPIONAMIDE

[75] Inventors: Alexander Mihailovski, Kensington; Raymond A. Simone, Walnut Creek, both of Calif.

[73] Assignee: Stauffer Chemical Company, Westport, Conn.

[22] Filed: Aug. 15, 1975

[21] Appl. No.: 604,968

[52] U.S. Cl. .............................. 260/559 B; 71/118; 260/561 HL; 260/559 P
[51] Int. Cl.² .............. C07C 103/22; C07C 103/30; A01N 9/20
[58] Field of Search ...................... 260/559 B, 559 P

[56] References Cited
UNITED STATES PATENTS

| | | | |
|---|---|---|---|
| 3,007,962 | 11/1961 | Metivier | 260/559 B |
| 3,010,996 | 11/1961 | Litvan et al. | 260/559 B |
| 3,106,564 | 10/1963 | Fleming et al. | 260/559 B |
| 3,213,140 | 10/1965 | Mills | 260/559 B |
| 3,383,411 | 5/1968 | Schultz et al. | 260/559 B |
| 3,446,811 | 5/1969 | Nordin et al. | 260/559 B |
| 3,480,671 | 11/1969 | Tilles et al. | 260/559 B |

FOREIGN PATENTS OR APPLICATIONS

| | | | |
|---|---|---|---|
| 1,443,110 | 5/1966 | France | 260/559 P |

OTHER PUBLICATIONS

Klosa, J. Prak. Chem., 19 (1963) pp. 45–54.

Primary Examiner—Arthur P. Demers
Attorney, Agent, or Firm—Joel G. Ackerman

[57] ABSTRACT

N,N-diethyl 2(α-naphthoxy)propionamide,

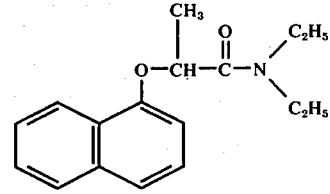

a useful herbicide, is produced by reaction of α-naphthol with an excess of N,N-diethyl-α-chloropropionamide or -bromopropionamide in the presence of an excess of alkali metal hydroxide. Unreacted amide is removed by vacuum stripping. The haloamide reactant is preferably formed by reaction of α-chloropropionic or α-bromopropionic acid with diethylamine in the presence of phosphoryl chloride.

22 Claims, No Drawings

PRODUCTION OF N,N-DIETHYL 2(α-NAPHTHOXY)PROPIONAMIDE

BACKGROUND AND PRIOR ART

As disclosed in U.S. Pat. No. 3,480,671, the compound N,N-diethyl-2(α-naphthoxy)propionamide has been found to be a useful herbicide. As described in that patent, it was prepared by reacting α-naphthol with N,N-diethyl-α-bromopropionamide in the presence of a 25% solution of sodium methoxide in methanol. The melting point of the product is given as 63°–64° C. However, preparation by this process produced a product in insufficient yield and with a purity below the minimum acceptable commercial level. It was subsequently proposed to produce this compound through the intermediate 2(α-naphthoxy) propionic acid,

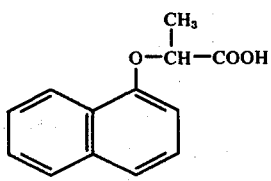

by reacting α-naphthol with α-chloropropionic acid. However, the production of this intermediate is somewhat expensive and in addition, the yields of the desired product from α-naphthol were at about the 50% level. Among the by-products were compounds having a furan-type ring condensed with the naphthalene ring, which are difficultly separable from the desired product.

It is an object of this invention to provide an improved process for the production of N,N-diethyl-2(α-naphthoxy) propionamide from α-naphthol.

A further object of this invention is to provide a process for production of N,N-diethyl-2(α-naphthoxy)propionamide of good purity and in acceptably high yield from α-naphthol.

A third object of this invention is to provide a process for production of N,N-diethyl 2(α-naphthoxy)propionamide from α-naphthol without requiring the use of sodium methoxide.

Other objects and advantages of this invention will be apparent from the description which follows.

SUMMARY OF THE INVENTION

In one aspect, this invention comprises a process for the production of N,N-diethyl-2(α-naphthoxy)propionamide comprising: (a) reacting diethylamine with a compound having the formula

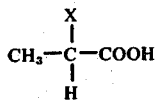

in the presence of phosphoryl chloride, to produce an amide having the formula

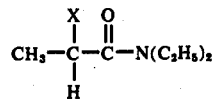

in which X is chloro or bromo; (b) reacting α-naphthol with an excess of the amide produced in step (a), in the presence of an excess of an aqueous solution of an alkali metal hydroxide and, (c) removing the unreacted amide from the reaction products.

In another aspect the invention herein comprises a process for the production of N,N-diethyl-2(α-naphthoxy) propionamide comprising (a) reacting α-naphthol with an excess of an amide having the formula

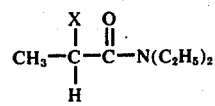

in which X is chloro or bromo, in the presence of an excess of an aqueous solution of an alkali metal hydroxide and (b) removing the unreacted amide from the reaction products.

DETAILED DESCRIPTION OF THE INVENTION

In essence the invention comprises the production of N,N-diethyl-2(α-naphthoxy)propionamide from α-naphthol by reacting the α-naphthol with an excess of either N,N-diethyl α-chloropropionamide or N,N-diethyl α-bromopropionamide. The chloro- or bromo-amide is preferably, though not necessarily, produced by reaction of the corresponding α-halocarboxylic acid with diethylamine in the presence of phosphoryl chloride. Reactions of this type are generally described in the article by Klosa, Journal für praktische Chemie, 19,45 (1963). The reaction of the α-naphthol with the amide is carried out in the liquid state by mixing the α-naphthol with an excess of the amide and an aqueous solution of an alkali metal hydroxide, preferably sodium hydroxide. The alkali metal hydroxide is utilized in an aqueous solution of between about 25 and about 50 weight per cent, and is present in an excess of between about 5 and about 60, preferably between about 20 and about 50 per cent, with respect to the α-naphthol. A two-phase system is formed, consisting of an aqueous layer comprising the alkali metal hydroxide and alkali metal salt of α-naphthol, and an organic layer comprising the desired product, solvent, unreacted α-naphthol and excess amide. Without being bound by theory, it is believed that the alkali metal salt of α-naphthol is the reactive species in this process. The amide is utilized in an excess of between about 5 and about 20 per cent, with respect to α-naphthol. Unconverted amide is removed from the reaction mixture by stripping with an inert gas, preferably steam, under high vacuum, preferably about 1 psia, after or during completion of the reaction. Generally, about 3 to 6 hours is required for completion of the reaction, usually about 4 hours. Surprisingly, the use of excess amide in the reaction substantially prevents the hydrolysis of amide to carboxylic by-products. The reaction is generally conducted at temperatures of about 90° to just below 100° C, and preferably between about 95° and about 98° C.

It has been found that the concentration and per cent excess of alkali metal hydroxide affects the conduct of the reaction between α-naphthol and the amide. The alkali metal hydroxide is preferably sodium hydroxide, though other alkali metal hydroxides, such as potassium hydroxide, lithium hydroxide, etc., may be utilized. Sodium hydroxide is preferred as it is more readily available and has the lowest cost. In general, within the ranges stated above, the reaction proceeded best at both a high concentration and high excess of alkali metal hydroxide.

In a preferred embodiment, the process is conducted utilizing toluene as a solvent. It has been found that the amount of toluene utilized, that is, the concentration of reagents, has an effect on the reaction rate. In particular, the less solvent used, the faster the reaction goes to completion. A good concentration is about 200 ml. toluene per mole of α-naphthol. At such a concentration, most of the reagents are consumed within four hours. Too much toluene can not only slow down the reaction rate but also result in foaming.

The desired product, N,N-diethyl 2(α-naphthoxy)-propionamide, has a melting point of 72°-73° C for technical grade and 75° C for the purer compound. Since the reaction between α-naphthol and the chloro- or bromo-amide is therefore conducted at a temperature above the melting point of the product, the reaction may be conducted without the use of an organic solvent since the product itself, being in the molten state, will serve as an acceptable solvent for the organic layer. However, the product obtained by this technique is not quite as pure as that obtained using an appropriate amount of toluene. Furthermore, the product obtained without use of a solvent shows additional high-boiling impurities when analyzed by gas chromatography.

In order for the desired product to be obtained in good purity and yield, the reaction between α-naphthol and the chloro- or bromo-amide must be carried out to completion and the excess unreacted amide, as well as other amide impurities, must be removed by thorough stripping. The reaction is preferably conducted batch-wise, being carried to completion in a batch reactor, the products being removed and unreacted amide stripped off in a vacuum stripper. If desired, however, the process can be carried out in one reaction vessel, in a continuous manner, under vacuum, to permit stripping of amide products, with the stripping rate of amide being controlled to maintain the desired excess.

Another advantage of the two-step process of first preparing the amide from the corresponding carboxylic acid and then reacting the amide with α-naphthol is that α-naphthol, which is the most expensive reagent, is used in the last reaction instead of the first reaction, as was the case in the prior art, when α-naphthol was first reacted to produce the intermediate 2-(α-naphthoxy)-propionic acid. In utilizing the process of the present invention, the yield of desired product based on α-naphthol is maintained at a higher value. In addition, it has been found that the intermediates produced in the present process are easier to analyze by gas chromatography than those heretofore produced. This permits better control in a commercial plant. Additionally, no furan-type impurities are formed with the present process.

Example

The following is an illustrative example of the preparation of N,N-diethyl 2-(α-naphthoxy)propionamide according to the present invention:

Into a 3 liter round bottom flask were placed 295 g (2.00 mole) of 98 per cent purity α-naphthol and 765 g (2.20 mole) of an N,N-diethyl 2-chloro-propionamide (based on 47 per cent assay) solution in toluene. The mixture was stirred and there was then slowly added 219 g (2.80 mole) of 51.2 per cent sodium hydroxide solution. The temperature increased from 22° to 47° C during the addition, and the solution turned black.

The solution was then heated to reflux (20 minutes) at about 95° C. When reflux began, sodium chloride began to separate out. Refluxing was continued for four hours, the reaction being monitored by gas chromatography. The reaction mixture was cooled to 50° C and 400 ml of water at this temperature was added. The aqueous phase, which was lighter in color than the organic phase, was separated. The organic phase, including the interface, was reheated to 50° C; a solution of 200 cc 25 per cent sodium hydroxide and 200 cc of hot water were added, and the phases separated again. A clean phase separation occurred. The solvent was evaporated first in a rotary evaporator at aspirator pressure and 80° C, then for two hours under high vacuum (22 mm Hg) at about 75° C. The liquid product was cooled until it solidified and ground to a fine powder. 543 g of product was recovered. The product was assayed at 94.9 per cent. Analysis by gas chromatography showed very few organics were present in the product, indicating that most of the impurities were from the presence of salt.

It is possible that modifications and variations of the invention as herein described will be apparent to those skilled in the art. Therefore the invention is not to be considered limited by the disclosure in the foregoing text, but only by the claims which follow.

What is claimed is:

1. A process for the production of N,N-diethyl 2(α-naphthoxy)propionamide, comprising:
   a. reacting diethyl amine with a carboxylic acid having the formula

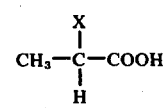

in which X is chloro or bromo, in the presence of phosphoryl chloride, to produce an amide having the formula

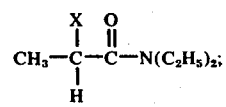

b. reacting α-naphthol with an excess of the amide produced in step (a), in the presence of an excess of an aqueous solution of an alkali metal hydroxide, and
   c. removing unreacted amide from the reaction products.

2. A process according to claim 1 in which the alkali metal hydroxide is sodium hydroxide.

3. A process according to claim 1 in which step (c) is carried out under vacuum.

4. A process according to claim 1 in which X is chloro.

5. A process according to claim 1 in which the amide is present in step (b) in an excess of between about 5 and about 20 per cent with respect to α-naphthol.

6. A process according to claim 1 in which the concentration of alkali metal hydroxide in the aqueous solution is between about 25 and about 50 weight per cent.

7. A process according to claim 1 in which the alkali metal hydroxide is present in an excess of between about 5 and about 60 per cent with respect to α-naphthol.

8. A process according to claim 7 in which the alkali metal hydroxide is present in an excess of between about 20 and about 50 per cent.

9. A process according to claim 1 in which step (b) is conducted at a temperature of between about 90° and just below 100° C.

10. A process according to claim 1 in which toluene is used as a solvent in step (b).

11. A process for the production of N,N-diethyl 2(α-naphthoxy)propionamide comprising (a) reacting α-naphthol with an excess of an amide having the formula

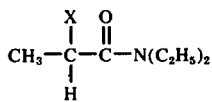

in which X is chloro or bromo, in the presence of an excess of an aqueous solution of an alkali metal hydroxide and (b) removing unreacted amide from the reaction products.

12. A process according to claim 11 in which the alkali metal hydroxide is sodium hydroxide.

13. A process according to claim 11 in which step (b) is conducted under vacuum.

14. A process according to claim 11 in which X is chloro.

15. A process according to claim 11 in which the amide is present in an excess of between about 5 and about 20 per cent with respect to α-naphthol.

16. A process according to claim 11 in which the concentration of alkali metal hydroxide in the aqueous solution is between about 25 and about 50 weight per cent.

17. A process according to claim 11 in which the alkali metal hydroxide is present in an excess of between about 5 and about 60 per cent with respect to α-naphthol.

18. A process according to claim 17 in which the alkali metal hydroxide is present in an excess of between about 20 and about 50 per cent.

19. A process according to claim 11 in which step (a) is conducted at a temperature of between 90 and just below 100° C.

20. A process according to claim 1 in which toluene is used as a solvent in step (a).

21. A process according to claim 6 in which the alkali metal hydroxide is present in excess of between about 5 and about 60 percent with respect to α-naphthol.

22. A process according to claim 16 in which the alkali metal hydroxide is present in an excess of between about 5 and about 60 percent with respect to α-naphthol.

* * * * *